Figure 2:
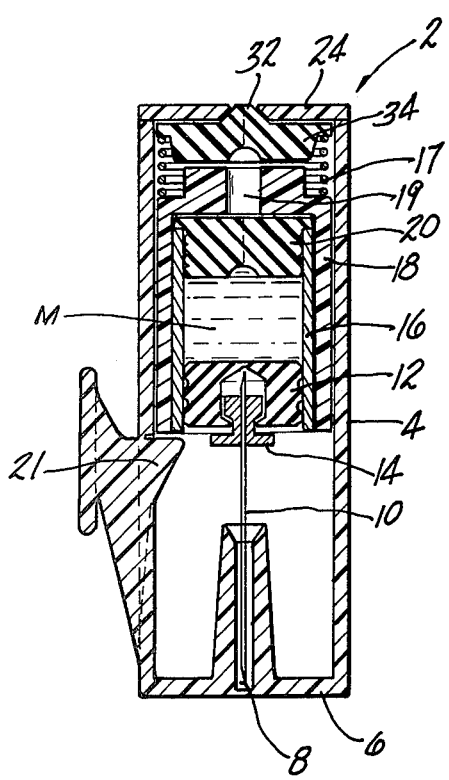

United States Patent [19]

Wardlaw

[11] 4,196,732

[45] Apr. 8, 1980

[54] AUTOMATIC DISPOSABLE SYRINGE AND METHOD OF FILLING THE SAME

[76] Inventor: Stephen C. Wardlaw, 128 Sunset Hill Dr., Branford, Conn. 06405

[21] Appl. No.: 21,483

[22] Filed: Mar. 19, 1979

Related U.S. Application Data

[63] Continuation-in-part of Ser. No. 972,756, Dec. 26, 1978.

[51] Int. Cl.² .............................................. A61M 5/00
[52] U.S. Cl. ............................ 128/218 F; 128/218 A; 141/330
[58] Field of Search ........... 128/218 R, 218 F, 218 C, 128/218 A, 218 G, 218 W, 215, 216, 234, 224, 272.1, 272.3; 141/2, 27, 329, 330

[56] References Cited

U.S. PATENT DOCUMENTS

| | | | |
|---|---|---|---|
| 2,667,164 | 1/1954 | Smith | 128/216 |
| 3,082,681 | 3/1963 | Petersen | 141/329 X |
| 3,238,784 | 3/1966 | Dorsey et al. | 141/329 X |
| 4,044,758 | 8/1977 | Patel | 128/234 |

Primary Examiner—John D. Yasko
Attorney, Agent, or Firm—William W. Jones

[57] ABSTRACT

An automatic disposable syringe which can be assembled completely, except for the medication, in a non-sterile environment. The syringe can then be sterilized and filled with medication in a sterile environment and packaged or otherwise sealed for use by the ultimate user.

9 Claims, 2 Drawing Figures

U.S. Patent    Apr. 8, 1980    4,196,732

4,196,732

AUTOMATIC DISPOSABLE SYRINGE AND METHOD OF FILLING THE SAME

This application is a continuation-in-part of my co-pending application, Ser. No. 972,756, filed Dec. 26, 1978.

There is a substantial need for an automatic, pre-dosed, discardable hypodermic syringe for use by trained and untrained persons. Such syringes are more desirable than conventional syringes which are filled manually from a vial of medication. Among the more desirable features found in the automatic syringes are the following: the dose of medication is accurately measured and pre-loaded in the syringe so that the chances of under or over-dosing the patient is eliminated; the syringe operates automatically so that the needle need not be manually inserted into the patient's body before the injection is made; and the automatic syringe can be constructed so that reuse of a once-used syringe can be prevented.

There is a relatively substantial body of prior art directed at the construction of automatic syringes. The prior art automatic syringes generally consist of a number of parts which must be assembled together to form the automatically operable device. The number of parts in a syringe can range from a relatively small number, as in the device disclosed in my co-pending application Ser. No. 972,756 referred to above, to a relatively large number for more complicated devices.

One problem which has been perceived in connection with the production of an automatic syringe relates to the need for sterility of internal components. This need dictates that the syringe be assembled and packaged in a sterile environment, generally referred to as a "clean room". The need to use a clean room for syringe assembly increases the capitalization of automatic syringe production and the cost of the syringe.

The syringe of this invention may be assembled in a non-sterile environment. The entire unit is assembled, except for the medication, and the assembled unit is then ready to be filled with medication by the filling process of this invention.

The unfilled assembled unit may be heat sterilized, or gas sterilized, a procedure which is not possible for a syringe which contains heat-sensitive medication. The sterilization step may be performed immediately prior to filling, or may be performed at a location remote from the filling station. In the latter case, the unfilled sterilized assembled unit will be sealed, either by virtue of its construction, tape strips, or by separate or bulk packaging to maintain the sterility of the interior of the unit.

It is, therefore, an object of this invention to provide an automatic, disposable hypodermic syringe which can be assembled, except for the medication dose, in an unsterile environment.

It is a further object of this invention to provide a hypodermic syringe of the character described which can be sterilized after assembly and prior to filling with a dose of medication.

It is an additional object of this invention to provide a hypodermic syringe of the character described which can be filled with a medication after the syringe has been assembled and sterilized without disturbing the sterility of the internal parts of the syringe.

It is yet another object of this invention to provide a method of filling a hypodermic syringe of the character described after the syringe has been assembled.

Figure 1:
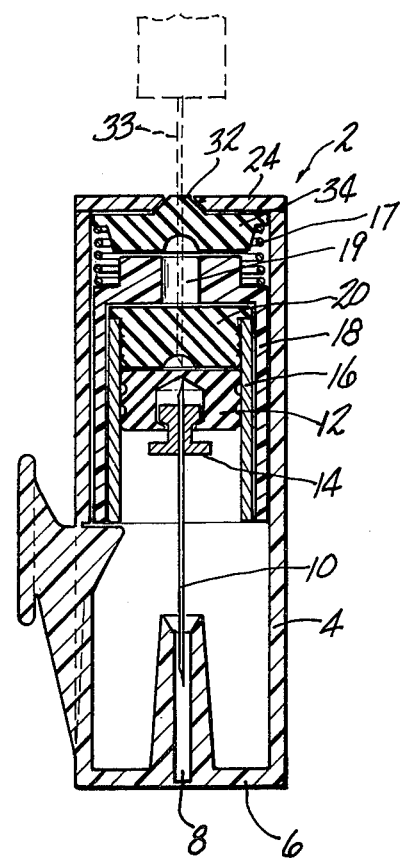

These and other objects and advantages of the invention will become more readily apparent from the following detailed description of a preferred embodiment of the invention taken in conjunction with the accompanying drawings, in which:

FIG. 1 is an axial sectional view of an embodiment of a syringe formed in accordance with this invention, the syringe being shown in an unfilled condition; and FIG. 2 is an axial sectional view similar to FIG. 1 but showing the syringe in its filled condition.

Referring now to the drawings, there is shown in FIG. 1 an assembled, but unfilled automatic syringe denoted generally by the numeral 2. The syringe 2 includes a housing 4 having a bottom end surface 6 which is placed against the patient's skin when an injection is administered. A needle port 8 extends to the bottom end surface 6 of the syringe 2. A needle 10 is disposed in the housing 4 aligned with the port 8, the needle 10 being shown in the drawings in a cocked position. The needle 10 is mounted on an elastomeric piston 12 by means of a ferrule 14. The piston 12 is telescoped in an ampoule 16 within the housing 2. The ampoule 16 is mounted in a carrier 18 which in turn is held in place against the bias of spring 17 by inward-protruding catch 21. This catch is of the break-away variety, and when the catch is withdrawn from the body 4 of the syringe, the carrier 18 and ampoule 16 are forced downward by spring 17, thus actuating the device and delivering the dose of medication. Further details of the construction and operation of the syringe are disclosed in my co-pending application Ser. No. 972,756, referred to above. It will be noted from FIG. 1 that the ampoule 16 is empty of medication, and that the piston 12 is telescoped well into the ampoule 16, there being a predetermined space between the inner surface of the piston 12 and the upper end of the ampoule 16. The upper end of the ampoule 16 bears an elastomeric, self-sealing end piece 20. The transverse portion of the carrier 18 is provided with a through passage 19. The upper transverse portion of the cap 24 is also provided with a through passage 32 which is sealed with an elastomeric member 34. It will be noted that the passages 19 and 32 are aligned with each other and substantially coaxial.

It will be noted that the syringe can be assembled to the degree shown in FIG. 1 in a non-sterile environment. The assembled syringes can then be shipped to various drug companies to be filled with whatever drugs are to be dispensed by it.

Either at the site of original assembly or at the filling facility, the syringes may be sterilized by heat, or other appropriate means. The sterilized syringes are then placed on or in a filling fixture which positions them for filling. If necessary, sterilization of the top surface can be repeated by such means as local surface heat, ultraviolet radiation, or the like.

Filling needle 33 (shown in phantom in FIG. 1) then enters the space between the top surface of the piston 12 and the lower surface of the ampoule top 20. The appropriate quantity of medication is dispensed, which forces piston 12 and needle 10 downward. The needle 33 is then withdrawn, and the elastomeric member 20 reseals the puncture hole made by the filler needle 33. The elastomeric member 34 also reseals itself when the needle 33 is withdrawn.

For some uses, elastomeric member 34 may not be used. Opening 32 can be covered by a perforable web or tape, or left open, sterility being provided by external packaging. After filling, opening 32 can be sealed (or re-sealed) by means of tape, heat-sealing, or the like.

The needle port 8 may be either formed with a small web as shown or may be covered by a perforable tape or may be left open if the unit is to be placed within a separate sterile container.

It will be noted that the specific release mechanism, e.g., the break-away release, is only one of many possible release mechanisms which may be used to automate the syringe, and does not limit the invention as regards its mode of filling with medication or the non-sterile assembly capabilities.

It will be readily appreciated that the syringe of this invention can be assembled in a non-sterile environment and later heat or gas sterilized prior to filling, and then filled while still sterile. The filled syringe is then packaged in a sterile pack for shipping, if not otherwise sealed. Thus, the syringe of this invention and the method of filling obviate the need to provide a sterile environment for assembling the syringe.

With the prior art automated syringes, the medication will be pre-loaded into the ampoule sub-assembly under sterile conditions, usually by a drug firm who specializes in the particular medication, and the filled ampoule will then be kept sterile and transported to the assembly site. The remaining parts of the syringe are then assembled under sterile conditions incorporating the sterile ampoule sub-assembly. A filled syringe cannot usually be heat or gas sterilized due to heat sensitivity of the medication.

It will be appreciated that the syringe of this invention permits central assembly by specialized facilities under non-sterile conditions, and then permits transport of the assembled units to different drug firms wherein my filling method can be used to load the different medications into the syringes.

Since many changes and variations of the disclosed embodiment of the invention may be made without departing from the inventive concept, it is not intended to limit the invention otherwise than as required by the appended claims.

What is claimed is:

1. In an improved automatic disposable hypodermic syringe of the type comprising a housing; a hypodermic needle disposed recessed within said housing; and a medicament container disposed in said housing; means for permitting filling of said medicament container with a medicament, said means comprising: a first opening in said medicament container; a second opening in said housing, said first and second openings being aligned; and an elastomeric member sealing at least said first opening, said member forming a self-sealing access into said medicament container through which a filler needle may be inserted via said second opening to permit injection of a dose of a medicament into said medicament container through the filler needle.

2. The syringe of claim 1, further comprising an elastomeric member sealing said second opening.

3. An improved automatic disposable hypodermic syringe comprising:
   (a) a housing;
   (b) first means in said housing for containing a dose of a medicament;
   (c) a hypodermic needle in said housing, said hypodermic needle being retracted within the confines of said housing;
   (d) spring means in said housing for driving said hypodermic needle to an injecting position wherein said hypodermic needle projects from said housing;
   (e) releasable catch means for holding said spring means in a cocked position;
   (f) means in said housing for pumping the medicament through said hypodermic needle responsive to release of said spring means from its cocked position;
   (g) said housing having one wall thereof formed with an opening therethrough;
   (h) said first means comprising an opening aligned with said housing wall opening; and
   (i) an elastomeric member sealing said first means opening, said elastomeric member forming a self-sealing access into said first means through which a filler needle may be inserted into said first means via said housing wall opening to permit an injection of a dose of a medicament into said first means through the filler needle after the syringe has been assembled.

4. An improved automatic disposable hypodermic syringe comprising:
   (a) a housing, said housing comprising means forming a needle port extending through one end wall thereof;
   (b) an ampoule assembly contained in said housing, said ampoule assembly comprising an ampoule for containing a dose of a medicament, and an elastomeric piston telescoped into said ampoule, said ampoule including an elastomeric member sealing one end of said ampoule, and said piston including a transverse wall part thereof closely adjacent to said elastomeric member;
   (c) a hypodermic needle recessed in said housing and aligned therein with said needle port;
   (d) a spring disposed in said housing for driving said hypodermic needle to an injecting position wherein said hypodermic needle projects from said housing through said needle port;
   (e) catch means for releasably holding said spring in a cocked position;
   (f) the other end wall of said housing comprising an opening aligned with said elastomeric member; and
   (g) said elastomeric member providing a self-sealing access into said ampoule through which a filler needle may be inserted via said opening to permit injection of a dose of a medicament into said ampoule through the filler needle after the syringe has been assembled.

5. An improved automatic disposable hypodermic syringe of the type comprising a housing; a hypodermic needle disposed recessed in said housing; and an ampoule disposed in said housing; means for permitting filling of said ampoule with a medicament, said means comprising: a first opening in one end of said ampoule; a second opening in one end of said housing, said first and second openings being aligned; a first elastomeric plug disposed in and sealing said first opening; and a second elastomeric plug disposed in and sealing said second opening; said first and second plugs forming a self-sealing access through which a filler needle may be inserted into said ampoule from outside of the syringe to permit injection of a dose of a medicament into said ampoule through the filler needle after the syringe has been assembled.

6. A method of filling a hypodermic syringe with a dose of a medicament, said syringe comprising a medicament-containing portion having an annular side wall, and first and second elastomeric members closing off and sealing opposite ends of said medicament-containing portion, at least one of said elastomeric members being slidable within said annular side wall, said method comprising the steps of:
    (a) puncturing the other of said elastomeric members with a filler needle;
    (b) injecting under pressure a measured dose of medicament through said filler needle into a space between said first and second elastomeric members and within said annular side wall, thereby causing said one of said elastomeric members to slide within said annular side wall away from said other of said elastomeric members; and
    (c) withdrawing said filler needle from said other of said elastomeric members, whereby said other of said elastomeric members self-seals the puncture passage therethrough created by said filler needle.

7. A method of filling a hypodermic syringe with a dose of a medicament, said syringe having one end wall thereof formed with an opening extending therethrough, and said syringe having an internal ampoule with an annular side wall, and first and second elastomeric members closing off and sealing opposite ends of said ampoule, at least one of said elastomeric members being slidable within said annular side wall of said ampoule, said method comprising the steps of:
    (a) inserting a filler needle through said end wall opening and puncturing the other of said elastomeric members with said filler needle;
    (b) injecting under pressure a measured dose of medicament through said filler needle into a space between said elastomeric members inside said ampoule thereby causing said one of said elastomeric members to slide within said ampoule side wall away from said other of said elastomeric members;
    (c) withdrawing said filler needle from said other of said elastomeric members and from said end wall opening whereby said other of said elastomeric members self-seals the puncture passage therethrough created by said filler needle; and
    (d) sealing said end wall opening.

8. The method of claim 7, wherein said end wall is made of plastic and said sealing step is accomplished by heat welding said end wall closed.

9. A method of filling a hypodermic syringe with a dose of a medicament, said syringe comprising a medicament-containing portion having an annular side wall, and first and second elastomeric members closing off and sealing opposite ends of said medicament-containing portion, at least one of said elastomeric members being slidable within said annular side wall, said syringe including an end wall having an opening therethrough sealed by an elastomeric seal, said method comprising the steps of:
    (a) puncturing said elastomeric seal and the other of said elastomeric members with a filler needle;
    (b) injecting under pressure a measured dose of medicament through said filler needle into a space between said elastomeric members and within said annular side wall thereby causing said one of said elastomeric members to slide within said annular side wall away from said other of said elastomeric members; and
    (c) withdrawing said filler needle from said other of said elastomeric members and from said elastomeric seal whereby said other of said elastomeric members and said elastomeric seal self-seal the respective puncture passages therethrough created by said filler needle.

* * * * *